US00PP24720P3

(12) United States Plant Patent
Davey et al.

(10) Patent No.: US PP24,720 P3
(45) Date of Patent: Jul. 29, 2014

(54) ***HELLEBORUS* PLANT NAMED 'ABCRD02'**

(50) Latin Name: *Helleborus×hybridus*
Varietal Denomination: ABCRD02

(76) Inventors: Rodney Davey, Devon (GB); Lynda Windsor, Devon (GB)

( * ) Notice: Subject to any disclaimer, the term of this patent is extended or adjusted under 35 U.S.C. 154(b) by 68 days.

(21) Appl. No.: 13/385,961

(22) Filed: Mar. 16, 2012

(65) Prior Publication Data

US 2013/0247266 P1 Sep. 19, 2013

(51) Int. Cl.
*A01H 5/00* (2006.01)

(52) U.S. Cl.
USPC ..... Plt./439

(58) Field of Classification Search
USPC ..... Plt./439
See application file for complete search history.

*Primary Examiner* — Susan McCormick Ewoldt
(74) *Attorney, Agent, or Firm* — Cassandra Bright

(57) ABSTRACT

A new *Helleborus* plant particularly distinguished by abundant purple flowers, upright plant habit and a vigorous growth habit, is disclosed.

1 Drawing Sheet

Genus and species: *Helleborus×hybridus.*
Variety denomination: 'ABCRD02'.

BACKGROUND OF THE NEW PLANT

The present invention comprises a new and distinct variety botanically known as *Helleborus×hybridus*, and hereinafter referred to by the variety name 'ABCRD02'. The new variety originated from a controlled hybridization conducted in February 2005 in Devon, United Kingdom, between female hellebore plant *Helleborus* nr. 'RD369HK01' (unpatented) and male hellebore plant *Helleborus* nr. 'RD959NB97' (unpatented). The seeds produced by the hybridization were sown in Devon, United Kingdom. A single plant selection was chosen for further evaluation and for asexual propagation in Devon, United Kingdom.

'ABCRD02' was subsequently asexually propagated by tissue culture in Aalsmeer, The Netherlands for at least 3 years. The present invention has been found to retain its distinctive characteristics through successive asexual propagations for at least 30 generations.

Community Plant Variety Rights (CPVR) for this variety were applied for in Europe on Jan. 25, 2012. 'ABCRD02' has not been made publicly available more than one year prior to filing of this application.

SUMMARY OF THE INVENTION

The following are the most outstanding and distinguishing characteristics of this new variety when grown under normal horticultural practices in Aalsmeer and Boijl, The Netherlands.

1. Abundant purple flowers;
2. Upright plant habit; and
3. A vigorous growth habit.

DESCRIPTION OF THE PHOTOGRAPH

This *Helleborus* plant is illustrated by the accompanying photograph which shows overall plant habit including blooms, buds, and foliage of the plant; the colors shown are as true as can be reasonably obtained by conventional photographic procedures. The photograph is of a whole plant about one-year-old, grown indoors in a glass covered greenhouse in Boijl, The Netherlands and Aalsmeer, The Netherlands.

DESCRIPTION OF THE NEW VARIETY

The following detailed description sets forth the distinctive characteristics of 'ABCRD02'. The data which define these characteristics were collected from asexual reproductions carried out in Aalsmeer and Boijl, The Netherlands. The plant history was taken on one-year-old plants grown indoors. Color readings were taken under artificial light. Color references are primarily to The R.H.S. Color Chart of The Royal Horticultural Society of London (R.H.S.) (2005).

DETAILED BOTANICAL DESCRIPTION

Classification:
- *Family.*—Ranunculaceae.
- *Genus and species.*—*Helleborus×hybridus.*
- *Common name.*—Christmas Rose.
- *Variety name.*—'ABCRD02'.

Plant:
- *Plant and growth habit.*—Upright and vigorous.
- *Propagation.*—In vitro propagation by tissue culture.
- *Height.*—25.0 cm to 35.0 cm.
- *Width.*—25.0 cm.
- *Time to initiate roots.*—6 weeks.
- *Time to produce a rooted cutting.*—Approximately 3 months.
- *Time to produce a finished plant.*—3 months.

Stems:
- *Shape.*—Round.
- *Length.*—3.0 cm.
- *Diameter.*—2.0 cm.
- *Internode length.*—0.1 cm.
- *Texture.*—Smooth.
- *Color.*—RHS 139A.

Leaves:
- *Type.*—Palmately compound.
- *Arrangement.*—Alternate.
- *Length.*—20.0 cm to 25.0 cm.

*Width.*—15.0 cm to 20.0 cm.
*Shape.*—Ovate to lanceolate.
*Apex.*—Obtuse.
*Base.*—Lanceolate.
*Margin.*—Serrate.
*Texture* (*both upper and lower surfaces*).—Smooth.
*Color.*—Immature leaf: Upper surface: RHS 139A. Lower surface: RHS 147A. Mature leaf: Upper surface: RHS 139A. Lower surface: RHS 147A.
*Leaflet.*—Leaflet number per leaf: 4 to 6. Leaflet shape: Obovate to somewhat ovate. Leaflet length: 6 to 10 cm. Leaflet width: 4 to 6 cm. Leaflet apex: acute. Leaflet base: between cordate and obtuse. Leaflet margin: serrate.
*Venation pattern.*—Longitudinal.
*Venation color* (*both upper and lower surfaces*).—RHS 137C.
*Variegation.*—Absent.
*Petiole.*—Length: 20.0 cm. Diameter: 0.6 cm. Color: RHS 147A and RHS 184B. Texture: Smooth.
*Petiolule.*—Length: 1.5 cm. Diameter: 0.5 cm. Color: RHS 147A and RHS 183C. Texture: Smooth.
*Stipules.*—Absent.

Inflorescence:
*Type.*—Loosely branched cymes.
*Shape.*—Loosely branched.
*Self cleaning or persistent.*—Persistent.
*Flowering habit.*—Vertical facing flowers above the foliage.
*Flowering season.*—January through March.
*Quantity of inflorescence on the plant.*—8 to 10.
*Fragrance.*—Absent.
*Lastingness of inflorescence on the plant.*—At least 2 months.
*Diameter.*—15.0 cm.
*Depth* (*height*).—25.0 cm to 30.0 cm.
*Individual flower.*—Flower depth or height: 0.8 to 1 cm. Average number of petals: 5. Color: RHS Purple N79C. Shape of apex: rounded. Shape of base: rounded, somewhat cordated. Margin: Entire.

Bud:
*Height.*—2.5 cm.
*Diameter.*—1.5 cm.
*Shape.*—Ovate.
*Color.*—RHS N79C.
*Texture.*—Smooth.

Bracts:
*Shape.*—Ovate.
*Quantity per inflorescence.*—2 to 10.
*Length.*—3.0 cm to 8.0 cm.
*Width.*—2.0 cm.
*Apex.*—Acute.
*Base.*—Ovate.
*Margin.*—Smooth.
*Texture* (*both upper and lower surfaces*).—Smooth.
*Color.*—Upper surface: RHS 139A. Lower surface: RHS 147A.

Peduncle:
*Shape.*—Round.
*Length.*—15.0 cm.
*Width.*—0.5 cm.
*Texture.*—Smooth.
*Color.*—RHS 187B.

Pedicel:
*Length.*—4.0 cm to 10.0 cm.
*Diameter.*—0.3 cm.
*Texture.*—Smooth.
*Color.*—RHS 187B.

Sepals:
*Quantity per flower.*—5.
*Shape.*—Orbicular.
*Length.*—4.0 cm.
*Width.*—3.0 cm.
*Apex.*—Rounded.
*Base.*—Rounded.
*Margin.*—Smooth.
*Texture* (*both upper and lower surfaces*).—Smooth.
*Color* (*both upper and lower surfaces*).—RHS N79C.

Reproductive organs:
*Stamens.*—Quantity per flower: Approximately 60. Color: RHS 155D. Filament length: 1.0 cm. Filament width: 0.05 cm.
*Anthers.*—Shape: Ovate. Length: 0.2 cm. Diameter: 0.1 cm. Color: RHS 157B. Pollen amount: Sparse. Pollen color: RHS 157B.
*Pistils.*—Quantity per flower: 5. Shape: Tuberculate. Length: 2.5 cm. Width: 0.1 cm. Color: RHS N79C.
*Stigma.*—Length: 0.2 cm. Width: 0.05 cm. Color: RHS N79C.
*Ovary.*—Shape: Ovate. Color: RHS 139A.
*Style.*—Style length: 0.5 to 0.7 cm. Style RHS color: RHS Red-Purple 71C.

Fruit and seed set: None observed.
Disease and insect resistance: No particular resistance or susceptibility observed.
Physiological characteristics: Frost tolerant to 15° C.

COMPARISON WITH COMMERCIAL VARIETY

'ABCRD02' differs from *Helleborus* variety 'ABCRD01' (U.S. Plant patent application Ser. No. 13/374,191) in that 'ABCRD02' has a flower bud color of RHS N79C (purple), whereas 'ABCRD01' has a lighter flower bud color of RHS 70B (red-purple). Additionally, 'ABCRD02' has both an upper and lower surface sepal color of RHS N79C (purple), whereas 'ABCRD01' has an upper and lower surface sepal color of RHS 70B (red-purple) and RHS 70C (red-purple), respectively.

'ABCDR02' differs from the seed parent as it flowers more abundantly and grows more vigorously. 'ABCDR02' differs from the pollen parent in producing flowers higher above the foliage and having a deeper flower color.

We claim:

1. A new and distinct variety of *Helleborus* plant as described and shown herein.

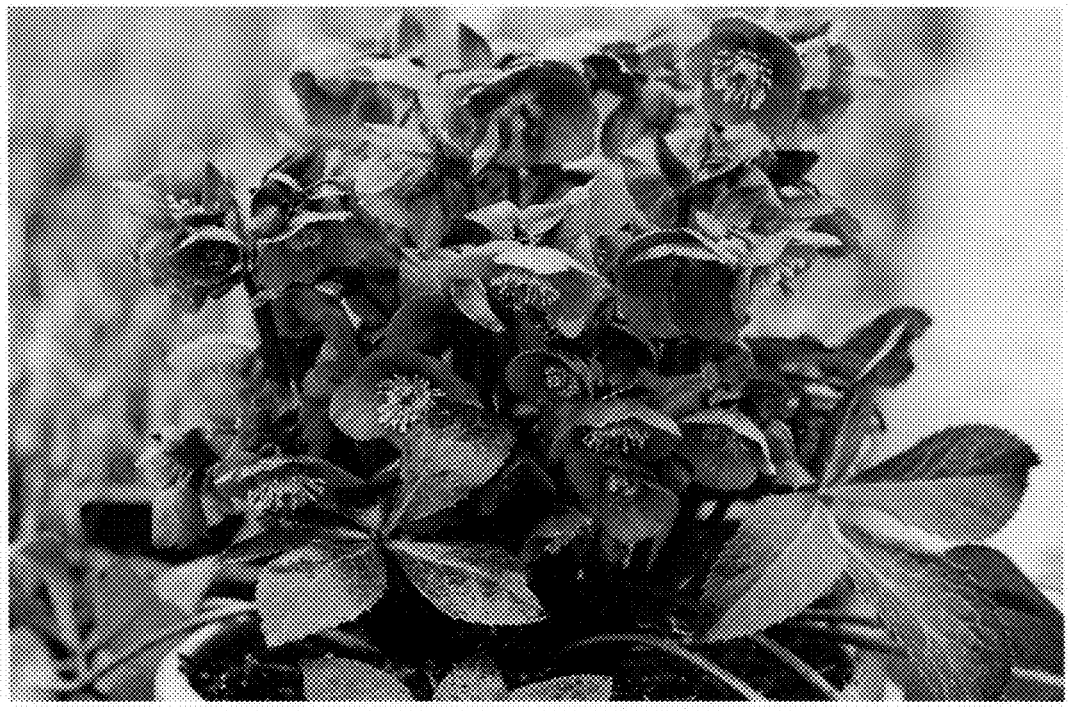

* * * * *